United States Patent
Krichevsky et al.

(10) Patent No.: US 7,510,864 B2
(45) Date of Patent: Mar. 31, 2009

(54) DECISION-MAKING SPECTRAL BIOREACTOR

(76) Inventors: Micah I. Krichevsky, 3023 Kramer St., Wheaton, MD (US) 20902; Steven A. Seiden, 236 G St., NE., Washington, DC (US) 20002; Louis W. Seiden, 11100 Rosemont Dr., North Bethesda, MD (US) 20852; Sam Butz, 19305 Poinsetta Ct., Gaithersburg, MD (US) 20879; Marc J. Epstein, 14 Beach Ave., Leonardo, NJ (US) 07737

(*) Notice: Subject to any disclaimer, the term of this patent is extended or adjusted under 35 U.S.C. 154(b) by 15 days.

(21) Appl. No.: 11/043,431

(22) Filed: Jan. 27, 2005

(65) Prior Publication Data
US 2005/0208473 A1 Sep. 22, 2005

Related U.S. Application Data

(60) Provisional application No. 60/539,194, filed on Jan. 27, 2004.

(51) Int. Cl.
C12M 1/36 (2006.01)
(52) U.S. Cl. .............. 435/286.5; 435/3; 435/288.7; 435/813
(58) Field of Classification Search .......... 435/286.5, 435/286.7, 288.7, 3, 813
See application file for complete search history.

(56) References Cited

U.S. PATENT DOCUMENTS

| | | | | |
|---|---|---|---|---|
| 5,262,961 A | * | 11/1993 | Farone | 702/23 |
| 5,424,209 A | * | 6/1995 | Kearney | 435/286.5 |
| 6,111,248 A | * | 8/2000 | Melendez et al. | 250/239 |
| 6,395,538 B1 | * | 5/2002 | Naughton et al. | 435/288.7 |

OTHER PUBLICATIONS

Arnold et al. 'Use of At-Line and In-Situ Near-Infrared Spectroscopy to Monitor Biomass in an Industrial Fed-Batch *E.coli* Process.' Biotechnology and Bioengineering. vol. 80, No. 4, Nov. 20, 2002, pp. 405-413.*

(Continued)

*Primary Examiner*—William H Beisner
(74) *Attorney, Agent, or Firm*—Novak Druce & Quigg, LLP

(57) ABSTRACT

This invention fills several voids in bioreactor technology that allows efficient connection of aspects of physical science (optics, electronics, physical chemistry, sensors) to aspects of microbial and cell culture physiology in a uniquely interactive manner. This is accomplished mathematically through decision making software that utilizes detected changes in the course of fermentation. Decisions are aimed at determining the optima for cellular growth, optimizing for production or degradation of metabolites or substrates, or determining the limits of growth under various combinations of conditions. The invention determines optima or limits in a manner more quickly and at less cost than traditional methods. The basis for the computer generated decisions may be first or second derivative changes observed such as inflection points, limits on allowable rates of change, or the like. The most common measured parameter controlling the decision making process is the optically observed growth of the cells (e.g. microbial, animal, or plant cell cultures) under study. Any other measurable parameter (e.g. pH, temperature, pigment production) may be used to control the process (i.e., the independent variable). This process and variations of this process on a laboratory scale are valuable for research and development, education, pilot plant models, and bio-manufacturing optimization, including scale up to production volumes.

14 Claims, 11 Drawing Sheets

OTHER PUBLICATIONS

Bird et al. 'Monitoring and Controlling Biocatalytic Processes.' BioPharm International. Dec. 2002, pp. 14-18,20,21.*

Cimander et al. 'Online monitoring of a bioprocess based on a multi-analyser system and multivariate statistical process modeling.' Journal of Chemical Technology and Biotechnology. vol. 77, 2002, pp. 1157-1168.*

Vaidyanathan et al. 'Assessment of Near-Infrared Spectral Information for Rapid Monitoring of Bioprocess Quality.' Biotechnology and Bioengineering, vol. 74, No. 5, Sept. 5, 2001, pp. 376-388.*

Junker et al. "On-line and in-situ monitoring technology for cell density measurement in microbial and animal cell cultures." Biprocessing Engineering. vol. 10 (1994), pp. 195-207.*

TAOS Product Brochure (2003) "Shaping the Future of Light Sensing Solutions". 8 pages.*

Levisauskas. "Inferential control of the specific growth rate in fed-batch cultivation processes." Biotechnology Letters, vol. 23 (2001), pp. 1189-1195.*

* cited by examiner

US 7,510,864 B2

DECISION-MAKING SPECTRAL BIOREACTOR

REFERENCE TO RELATED APPLICATIONS

This application claims priority to U.S. Provisional Application Ser. No. 60/539,194, entitled "Interactive Physiologic Control Fermentation Processes Using Real Time Decision Parameters Based on Data from Optical and Electronic Sensors in a Bioreactor" filed Jan. 27, 2004, the entire disclosure of which is hereby incorporated by reference.

BACKGROUND OF THE INVENTION

1. Field of the Invention

The present invention concerns a bioreactor device and computer methods of utilizing the device to monitor, analyze and control the course of growth of cells. Further, the invention concerns automated flexible modification of control parameters during the growth of the cells based on data obtained from sensors. The data discloses both continuous and transient growth effects. The modifications during growth can determine optimum conditions for growth or, conversely, conditions limiting growth.

2. Description of the Background

Prediction of the course of cellular growth in fermentations (biogas, biomass, bioconversions, bioremediation, foods/feed, pharmaceuticals/medicines) is a complex process requiring knowledge and investigation of many basic physiologic parameters. Historically, the effect of physiologic parameters such as temperature, salinity, nutrients, cofactors, inhibitors, or pH may involve independent measurement. For example, normally an investigator places a series of individual cultures in incubators set at a series of temperatures. Investigation of multiple parameters and their interactions may involve a multivariate approach. The same is true of the other parameters. In the strict sense, these experiments only determine the "best" initial condition. They do not actually measure the graded effect of change during growth.

Much of traditional microbial or cellular physiology involved elucidating the individual steps in the metabolism of a substrate and combining these steps into a pathway. Isotope tracing and genetic mutation were used to determine if the pathway actually worked. Investigations of the physiology of systems under growing conditions were largely ballistic in design, i.e., once the fermentation was started with a set of initial parameters, no changes were made and the results landed where they might. This was true of both closed systems and to a lesser extent to flow systems such as chemostats. Even today, most fermenters or bioreactors sold as having computer control are essentially analog or digital set point devices with the computer able to operate the controls. Desired changes after growth initiation may involve operator intervention. The present state of fermentation art largely involves empirical study of the effects of varying a single parameter during the course of fermentation.

The current state of the art in determining the course of cellular growth is to measure a single parameter such as optical density at fixed wavelength, capacitance measurements, and production of acid, redox potential, radio-frequency dielectrics, luminescence or fluorescence. Where optical techniques are used, the wavelengths are limited to a narrow band relative to the complete spectrum.

A number of commercial instruments utilize such single parametric measures such as:

The Aber Instruments Limited Model 220 biomass monitor which uses radio-frequency dielectrics.

The FOGALE Nanotech Company BIOMASS SYSTEM® is an on-line measurement instrument for determination of viable cell concentration using capacitance technology.

The Turner Designs algaewatch is an on-line monitor that detects algal biomass through chlorophyll fluorescence.

The Sartorius BBI Systems GmbH (BBI) (former B. Braun Biotech International GmbH) FUNDALUXr II system is an absorption-based photometric probe, designed for use in bioreactors and fermentors. The system uses a probe inside the culture vessel, which operates according to the transmittance principle with a wave length in the near infrared (NIR) range.

The optek-Danulat, Inc. Real-time biomass concentration probes use near infrared absorption. The series of bioprocess analyzers were designed specifically to integrate easily into existing bioreactors and fermenters.

All of the above instruments can monitor cell concentration and have some computational capacity. None of them use the information gathered in a control loop to modify the course of the fermentation.

U.S. Pat. No. 6,673,532 to Rao, uses non-invasive optical chemical sensing technology wherein an optical excitation source excites an optical chemical sensor. This system relies on single excitation wavelength bands and specific chemical sensor bands to monitor growth in small parallel vessels (e.g., 96 well plates).

With the exception of the system described by Rao, all the above instruments utilize a probe inserted in the fermentation vessel. The first use of such a probe was described in 1971 (Robrish, S. A., LeRoy, A. F., Chassy, B. M., Wilson, J. J., and Krichevsky, M. I., Use of a fiber optic probe for spectral measurements and the continuous recording of the turbidity of growing microbial cultures. Appl. Microbiol., 21: 278-287 {1971}). Later, a prototype autoclavable light probe to measure the concentration of bacterial mass was developed. In the 1971 paper, the simultaneous production of acid and the increase in biomass by a homolactic *streptococcus* was demonstrated.

In the above examples, the information produced by the probes or chemical sensors are usable for the operator to change parameters. None provide computer algorithms to automatically direct changes towards specific physiologic goals.

SUMMARY OF THE INVENTION

The present invention overcomes problems and disadvantages associated with current strategies and designs and provides new tools and methods for determining and controlling fermentation of bacteria, cells and other fermentable materials.

One embodiment of the invention is directed to digitally-controlled devices for determining and controlling cell growth or growth rate of cells in a fermentation vessel under transient conditions and in real time. The preferred device comprises: a computer for acquisition of digital and analog data from multiple sensors; interface electronics between the computer and instrumentation that provides power for switches and digital signals for control; input channels for sensor signals, either in the body of said computer or as an external device with a digital pathway; sensor inputs including at least a full-spectrum probe spectrometer and pH and temperature sensors; a temperature control device; a stirring mechanism capable of completely mixing contents of said fermentation vessel; one or more variable-intensity, broad-spectrum light sources that radiate in at least the visible spectrum; and ports within said fermentation vessel for insertion of said instrumentation. In this embodiment, a sensor is any device which can provide data, either internally or externally to the bioreactor chamber, on the contents and progress of the fermentation.

The device of the invention may have the digital pathway selected from the group consisting of a USB, a firewire, a serial connection, and a parallel connection, wherein the full-spectrum probe spectrometer detects visible, near infrared or near ultraviolet. The temperature control device may be a thermo-electrical heater or cooler, a resistance heater, or a double-jacket on the fermentation vessel for circulation of temperature controlled liquid. The stirring mechanism preferably comprises a variable speed controllable by computer, such that the stirring mechanism is capable of completely mixing the contents of said fermentation vessel in two seconds or less and said contents comprise a volume of at least 1 liter. Preferably, the one or more variable-intensity, broad-spectrum light sources further radiate ultraviolet and near-infrared spectra.

Another embodiment of the invention is directed to methods for determining and controlling cell growth or growth rate of cells in a fermentation vessel under transient conditions and in real time. Preferably, these methods involve supplying media containing cells to the fermentation vessel of the device of the invention; culturing the cells within the fermentation vessel; and determining and controlling the cell growth or growth rate of cells in the fermentation vessel. The method may further comprise supplementing the combination of sensors with combinations of additional sensors, wherein the additional sensors are selected from the group consisting of cation electrodes, anion electrodes, immobilized enzyme electrodes, redox potential electrodes, sensors that yield an electrical signal for data acquisition, and combinations thereof. Preferably, the method may further comprise computer controllable digital or analog pumps for addition or removal of fluids, wherein the digital or analog pumps may be piston pumps, peristaltic pumps or combinations thereof. The method may further comprise gas lines for introducing sterile or non-sterile gas into the head space of the fermentation vessel or into the contents of the fermentation vessel. The method may further comprise controlling the kinetics and metabolic processes of said cell growth or growth rate of cells with a computer, wherein the computer compiles digital and analog data from said combination of sensors. Preferably, the method may further comprise data smoothing of electronic and fluid mixing noise in real time allowing acquisition of smoothed data from input channels, inputting sensor data as a control parameter, recording digital data, both input and output to and from the computer in a database, rapidly acquiring multiple full spectra during a fermentation at a rate sufficient to detect transient spectral changes in the course of a fermentation, calculating optical density at all measured wavelengths, and detecting and recording changes in concentration of luminescent materials concurrently with light absorbing or scattering materials, wherein said luminescent material and said light absorbing or scattering materials are within the fermentation vessel, in real time.

Other embodiments and advantages of the invention are set forth in part in the description, which follows, and in part, may be obvious from this description, or may be learned from the practice of the invention.

DESCRIPTION OF THE INVENTION

For thousands of years, fermentation techniques played a central role in producing products of food and fiber. Initially, crude control of the fermentation processes yielded products of widely varying quality. Later, considerable progress in quality control improved quality. These improvements facilitated the later use of fermentation technology for production of solvents, pharmaceuticals, bioconversions, biomass, etc. Applying aspects of fermentation technology to animal and plant cell culture extended the utility and importance of such technology.

Figure 1:
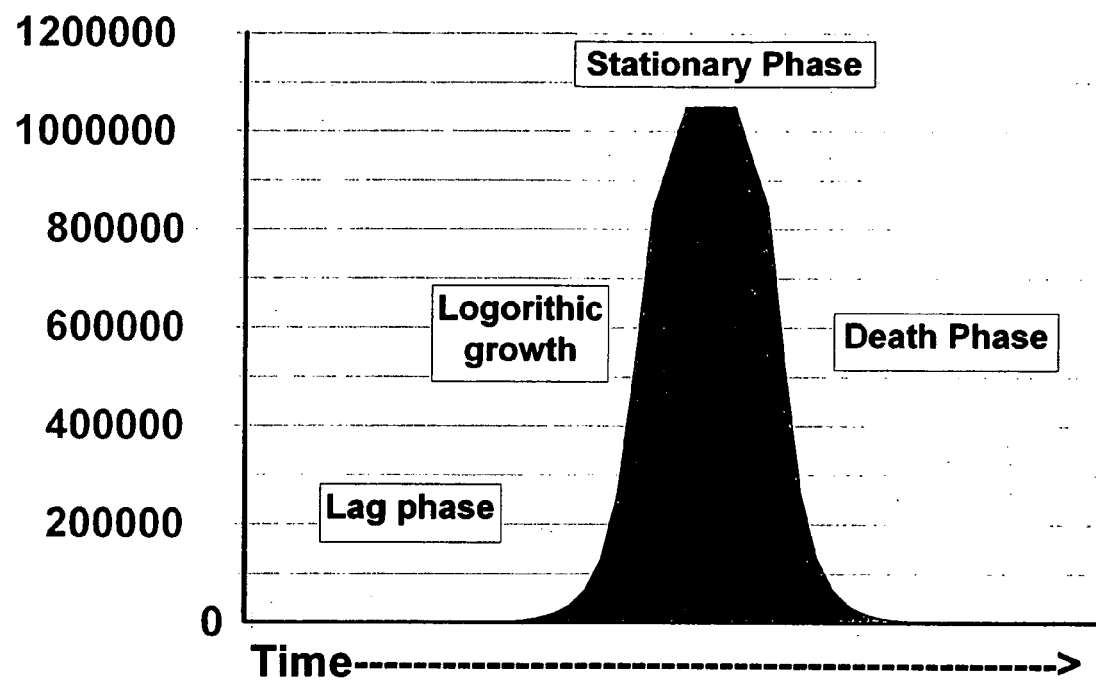
FIG. 1. Idealized growth cycle.

FIG. 1 illustrates the classic kinetics of organism growth and death in fermentation. Upon introduction into a new medium, the cells adjust to the new conditions before reproducing (lag phase). The cells start to reproduce at a rate which transitions into an exponential rate (logarithmic growth). When some condition becomes limiting such as utilization of a key nutrient, the growth rate slows down. The cells begin to die. The population reaches a peak concentration of cells in which the rate of formation of new cells equals the death of old cells (stationary phase). The death rate becomes increasingly faster than the formation of new cells in the death phase. Finally, the no new cells are formed. The exponent for plotting the rate of growth is optional. The most common ones are to the bases 10, e, or 2. If the base 2 is used, the slope of the line yields the generation time of the cells, i.e., the amount of time for the population to double.

Recently, the importance of knowing the limiting factors of growth increased with considerations of space science and bioterrorism. These latter aspects lend themselves to gaining knowledge by fermentation techniques. However, the basis for control of the course of the fermentations is largely empirical through trial and error experiments and observation. Optimum conditions for growth, yields of products or determination of the limits of growth in fermentations are dependent upon many, possibly interacting, variables.

Figure 2:
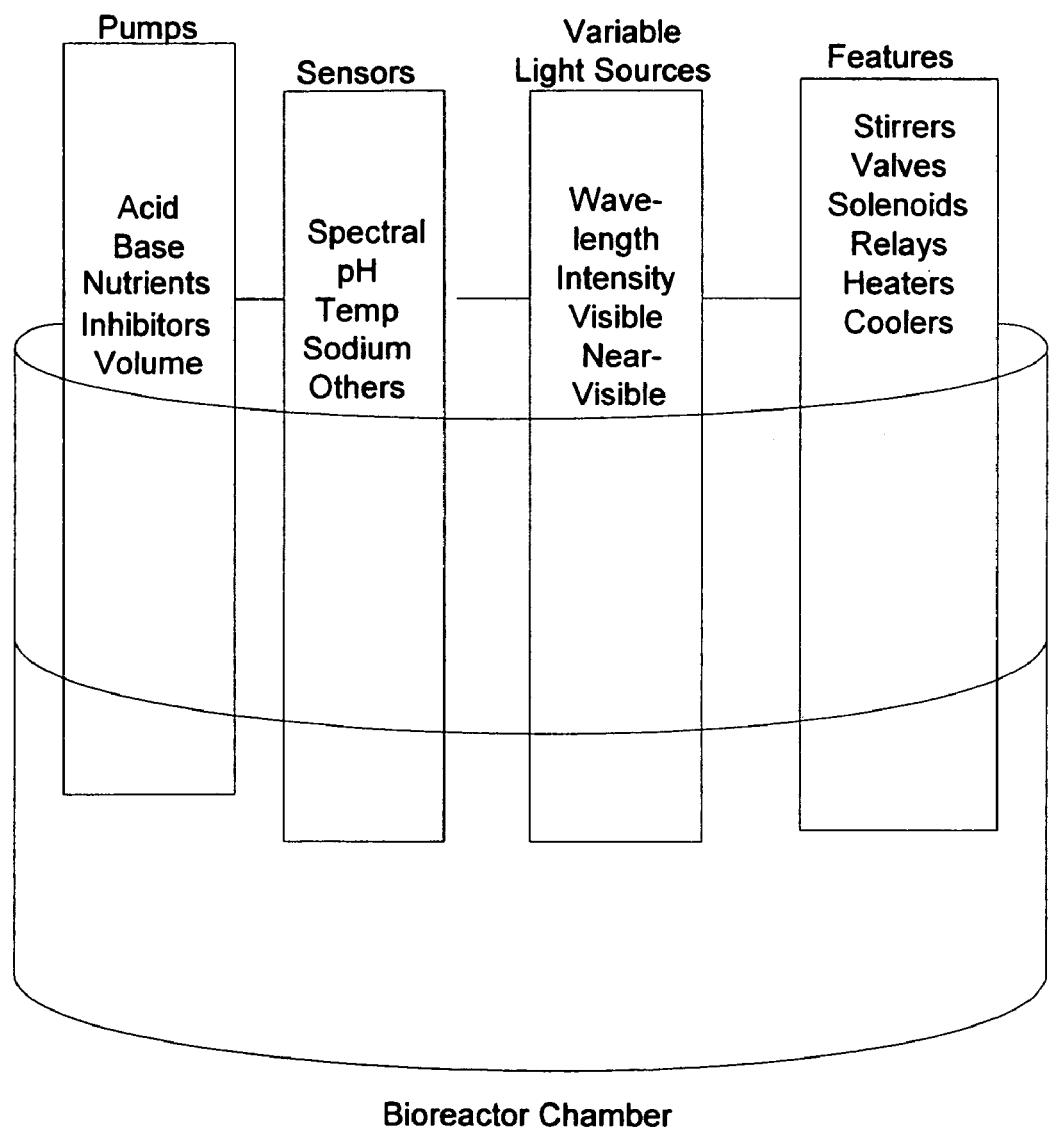
FIG. 2. Schematic diagram of the major components of the bioreactor.

Automated studying and controlling the details of cellular growth physiology under varying conditions involves a very flexible bioreactor (schematically illustrated in FIG. 2) with complete digital control of material addition and removal as well as data acquisition and operator interaction. We have built such a bioreactor which facilitates such basic determinations as finding the optimum or limits of growth temperature or pH in a single growth session. Multivariate experiments such as efficiently determining the interaction between temperature, pH, salt concentration and growth rate would be done efficiently. Many other parameters such as iron-chelating pigments production by pathogenic pseudomonads (*Pseudomonas aeruginosa*, causing cystic fibrosis) are concurrently measurable. We can determine both the optimum and limiting conditions of growth, product or toxin production.

This application presents such a multiphasic approach for acquiring and integrating the varied information necessary in such empirical determinations. The system uniquely controls a novel digitally operated analytic bioreactor using real time data acquisition sensors. Sensor inputs include, at least, but not limited to, a full spectrum (visible, near infrared and near ultraviolet) probe spectrometer and pH and temperature sensors. Supplementing the minimum sensors are combinations of other sensors from the group of various specific cation and anion electrodes, immobilized enzyme electrodes, redox potential electrodes and other sensors yielding an electrical signal for data acquisition.

The sensors provide information for the computer to instruct various pumps, light sources, heating or cooling devices, stirrers, or gas valves. While the various devices largely are not unique, their flexible combination is new. The software controls the course of a fermentation based on the data provided by the sensors, thus providing data control management and analysis for monitoring and varying the course of the fermentation.

Data acquisition from, and direct digital control (DDC) of, highly instrumented small bioreactors using an on-line computer is advantageous for such optimization. The advantages of DDC are:

1. Data on many variables can be collected conveniently, and at almost any frequency, allowing discovery and better study of rapid transient phenomena.

2. Because of the larger data base that can be obtained, more accurate (statistical) analysis is possible. This makes it easier to differentiate among mathematical models that might describe a particular aspect of the fermentation.

3. Complex and interactive control becomes possible. Process parameters can be changed continuously or abruptly under program control as user-specified functions. These functions can be flexible, since the user interacts with the program, and may change them while the experiment is in progress as desired.

Using the example of lactic acid production by a homolactic dairy bacterium, a pH electrode would send the current pH to the computer which in turn, calculates the amount of acid or base needed to either maintain the pH, or, more importantly, the amount necessary to achieve the desired rate of change of pH vs. time. The rate of pH change could follow any function desired (monotonically increasing, step, oscillating, and the like). The computer would keep track of the amount of acid or base added with time. The record of addition represents the dynamics of acid production. By combining the pH control with programmed temperature variation, the interaction between pH and temperature as they affect growth rate (tracked by the optical density) is measurable.

The sensors and pumps necessary to accomplish a wide variety of such interactions are available. Further, the computer can control parameters based on increasing the yield of variously, end or intermediate product production, cell mass (if cells are needed for scale up inocula), growth rate, etc. Maximizing yield of an intermediate may well result in decreasing the growth rate and/or cell yield. However, temperature effects must take into account the hysteresis following a command to change due the heat capacity of the liquid and the bioreactor itself. A key component of the fermentation system is the optical probe to continuously measure cell density and other parameters in situ.

Figure 3:
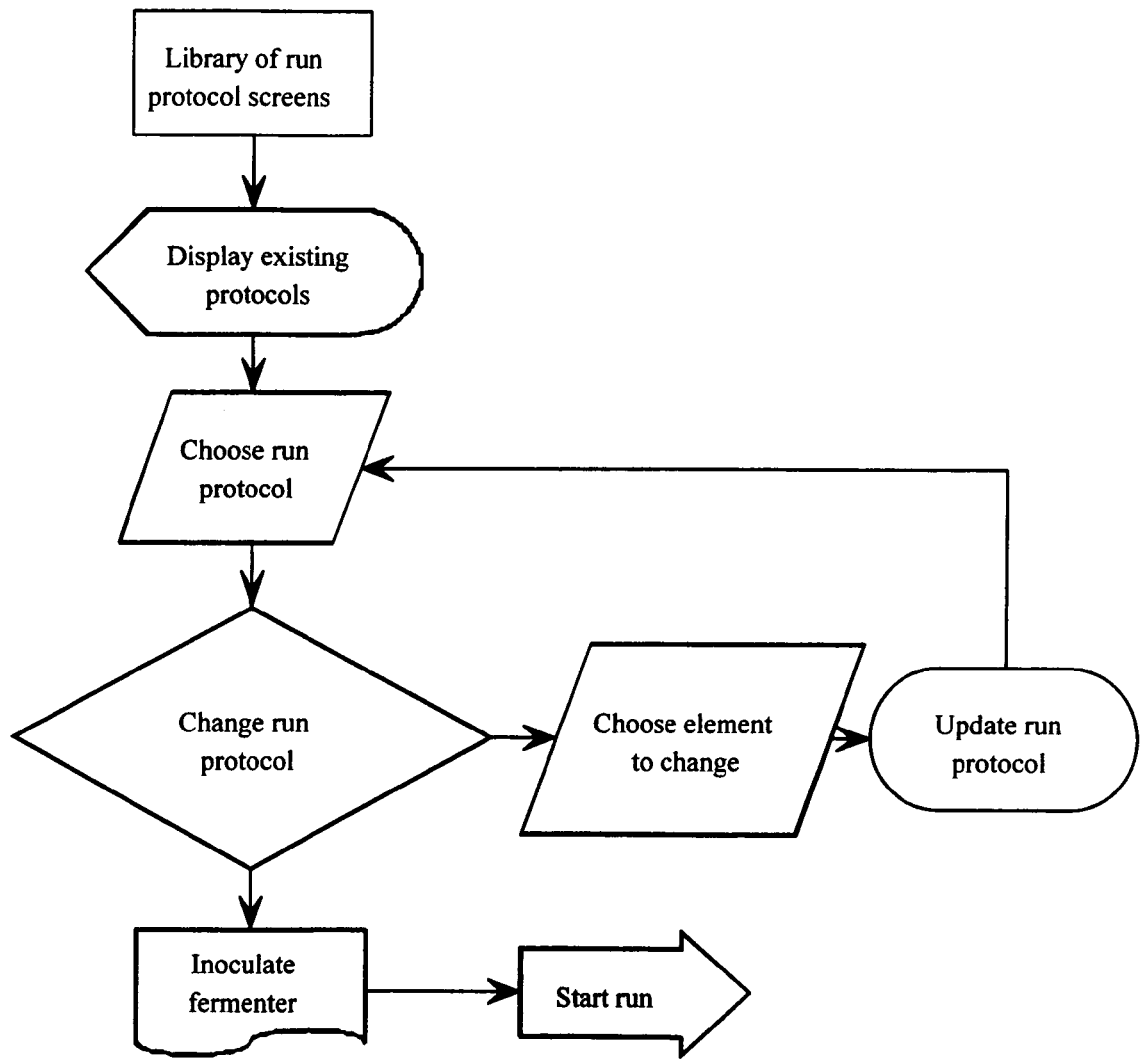
FIG. 3. Overview schematic of the initiation of fermentation.

The ideal test protocols develop information on the interactions, in real time, among many parameters such as pH, temperature, nutrient flux, gas diffusion rates, and so on. We know little about the physiologic effects of modifying combinations of such parameters during the course of fermentation. If comprehensively done, determining optimal or limiting conditions can involve statistical analysis and mathematical modeling of the multidimensional information. FIG. 3 diagrams the overall model for initiating automated fermentation.

Initial conditions: The first step is to decide the desired protocol and result of the fermentation.

Figure 4:
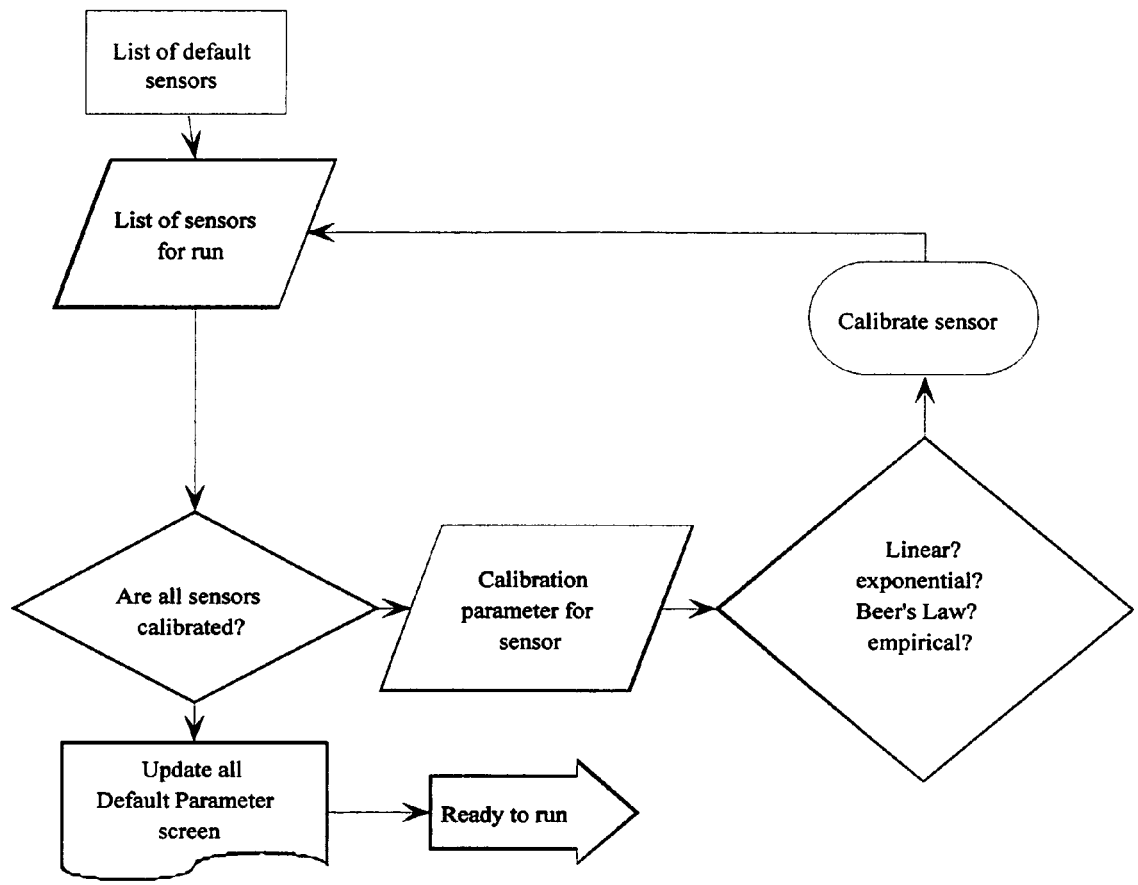
FIG. 4. Generalized flow for establishing calibrations for all sensors.

The operator of the system chooses initial parameters as well as the decisions to be made by the computer as the fermentation proceeds. FIG. 4 diagrams the general setup process for sensors. Before a protocol can be chosen, the various sensors must be calibrated and be so certified as suitable for inclusion in a particular fermentation protocol.

The optical system and the decision algorithms pH indicator dyes, such as Phenol Red, are valuable for full spectrum testing, to check the calibration, decision algorithms, integrity and repeatability of the system. The decision algorithms are verified by raising the pH of the phenol red solution under computer control to find a maximum value of an intermediate wavelength between the frankly yellow and frankly red extreme forms of the dye.

Figure 5:
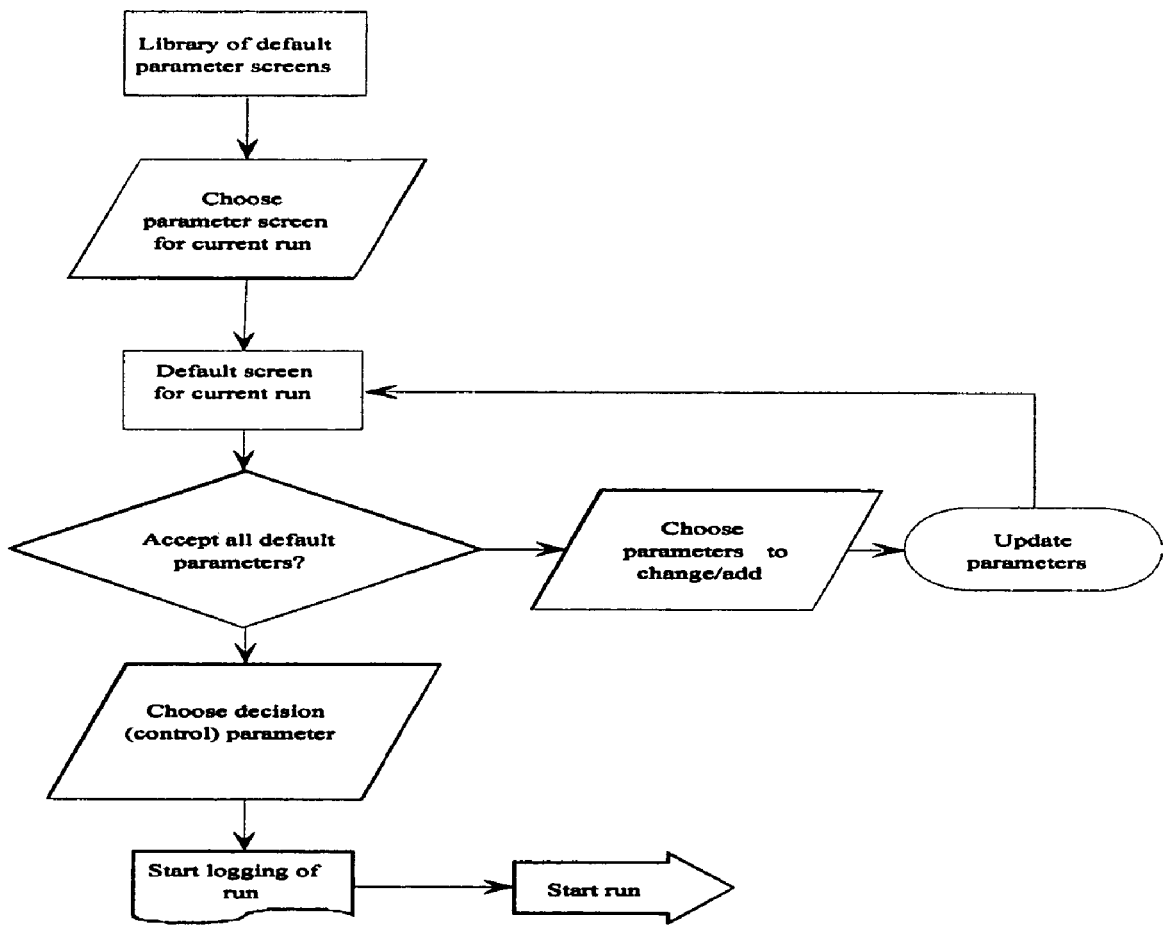
FIG. 5. Procedure for setting fermentation parameters for automated process.

After entry of any new calibration values into a master file of calibration values, the operator chooses a protocol (FIG. 5) for the fermentation run from a library of protocols. The protocol library evolves as new protocols are devised. Any protocol may be modified and used once or stored in anticipation of reuse.

Figure 6:
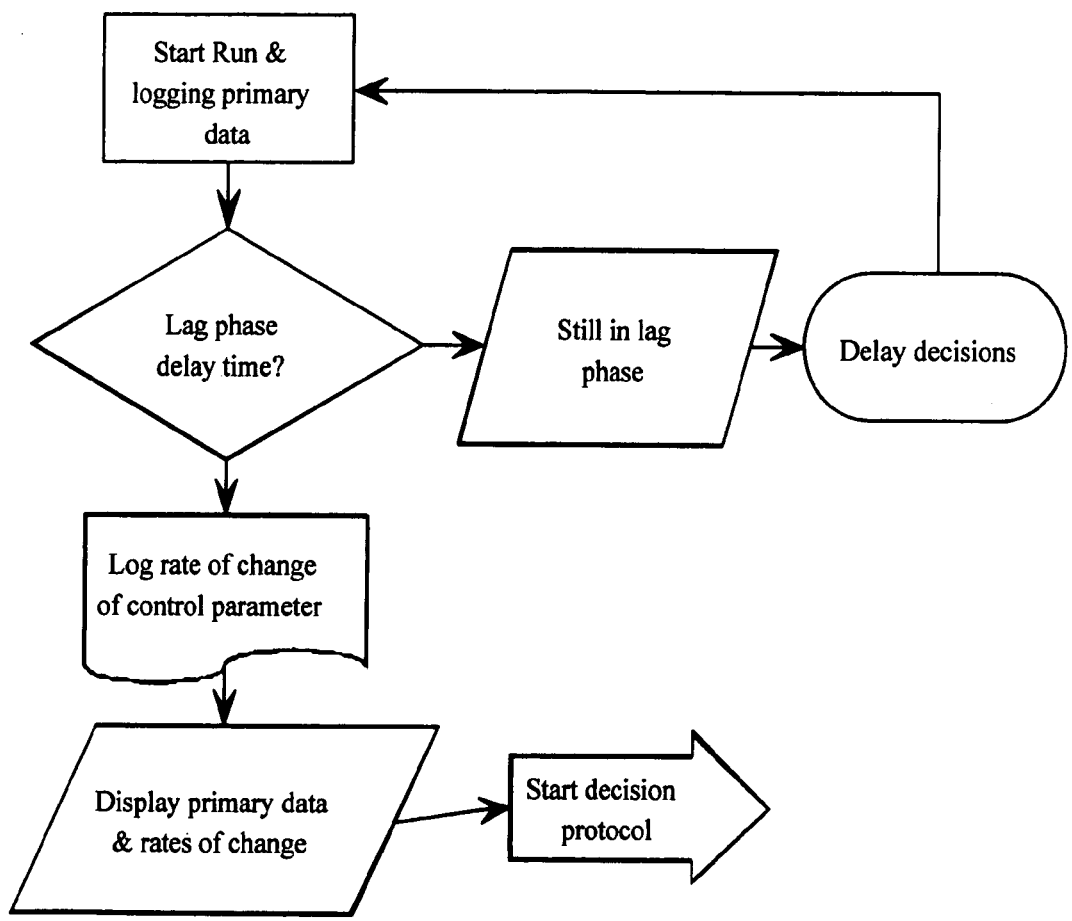
FIG. 6. Outline of algorithm for delay of invoking decision protocol due to lag phase of growth.
Figure 7:
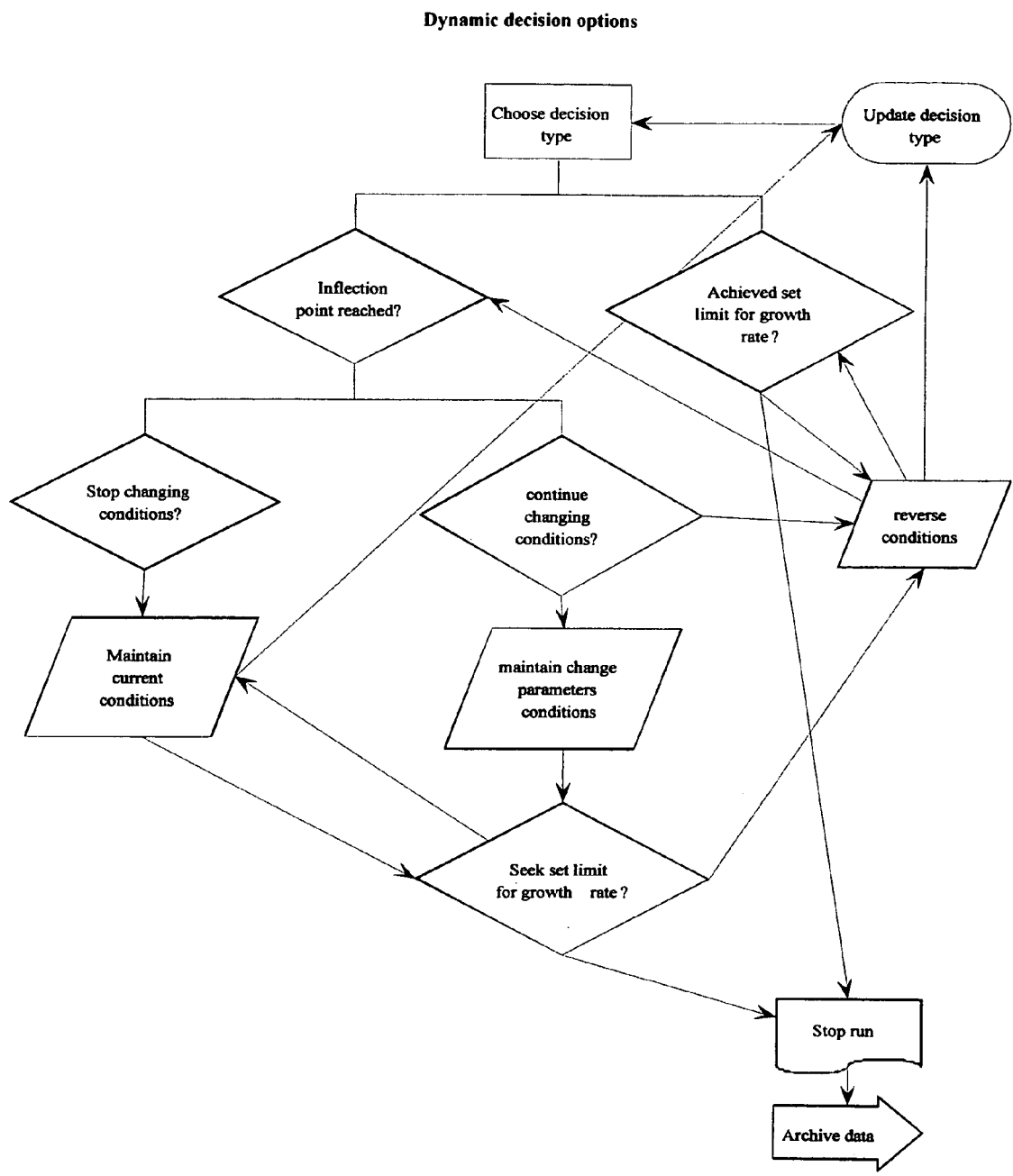
FIG. 7. Algorithm for real time automated decisions.

When any fermentation starts, the cells initially grow very slowly if at all. The classic "lag phase" (FIG. 1) is tracked and a threshold established for the initiation of automated decision making by the computer (FIG. 6). Without such a threshold, there is a risk of false positive maxima due to low level noise in the data.

Once the threshold value is reached, the decision protocol starts. Prior to the start of the fermentation, the operator chooses the sequence of decisions the computer must follow FIG. (7). These may be decisions such as:

finding the optimum growth rate or product production by detecting an inflection point;

confirming the optimum value by oscillating the control parameter;

finding the limit of growth by approaching a low growth rate tolerance value;

changing to a new control parameter after an optimum is reached for determining interactions;

combining various decision criteria; and looping back to the initial decision protocol for multiple sub protocols.

The operator may modify or add to the protocol during the fermentation by invoking an override function.

Figure 8:
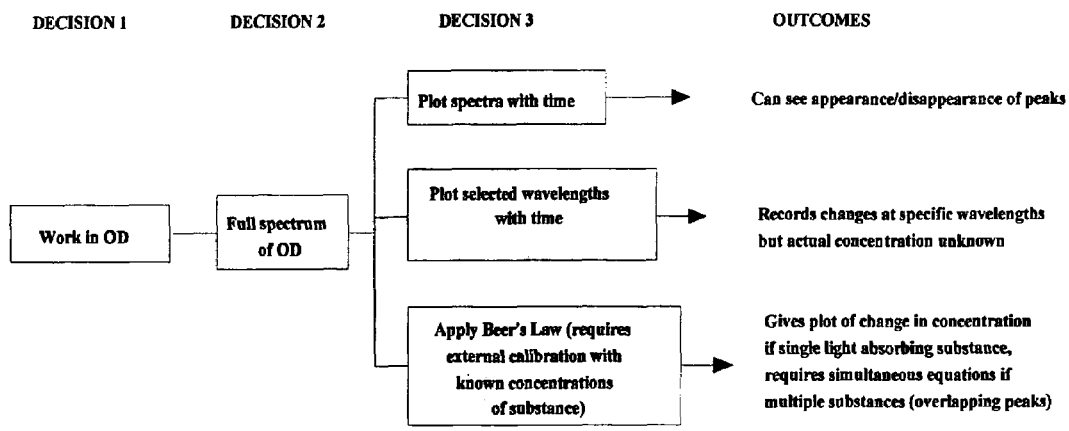
FIG. 8. Outcomes of decisions evolving from Optical Density calculations.
Figure 9:
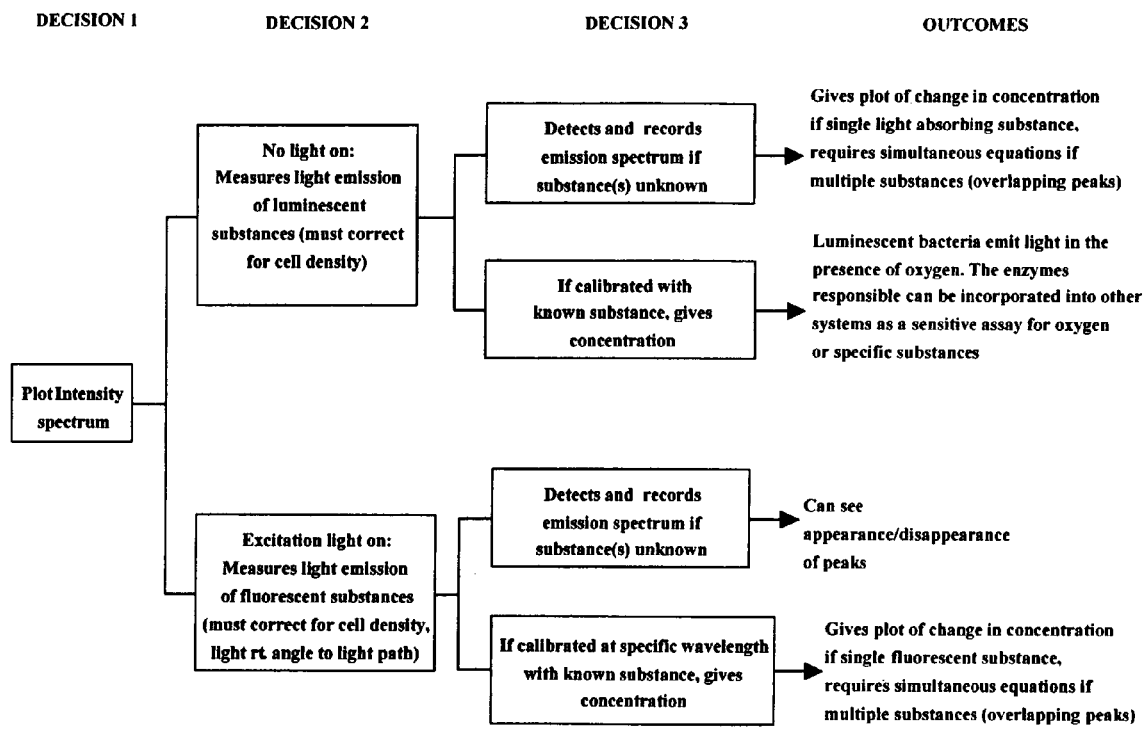
FIG. 9. Outcomes of decisions evolving from intensity spectrum calculations.

The optical spectrophotometer probe is essential to all uses of the system. In most fermentations, the cell growth and rate thereof or the production of optically active substances are critical to the decision making process by the computer. Even in those situations where the optical information is not used to trigger decisions (e.g., acid production is the trigger), following the growth of the cells is necessary to determine if the rate of growth of cells is directly coupled to the non-optical trigger parameter. FIGS. 8 and 9 present the outline of the uses of the optical probe for the acquisition of data on optical density, luminescence and fluorescence.

Determination and control of physiological parameters such as optima and limits of growth or production of cells or materials in liquid media have severe constraints. These include complexity, time, and cost. Two main historical methods for determining optima and limits are 1) using a series of cultures of the cells incubated with increasing amounts (e.g., pH, salt, nutrients) or physical conditions (e.g., temperature, light) of test variables, or 2) making many repeat experiments in fermentation bioreactors and varying the conditions in each experiment. The present invention overcomes these difficulties by constructing a bioreactor with a flexible array of sensors, pumps, stirrers, gas lines, temperature controllers, fermentation vessels, etc. and a computer with interface electronics for multiple function data acquisition and real time control.

The working system demonstrates the functionality of the bioreactor design. Interacting sensors monitor and control the growth rate of cells through optical density and spectral interpretation. The independent variables and dependent variables change as the experimental objectives change. The growth and growth rate are influenced by many factors or parameters that can be monitored and in some instances controlled. Two of the most important of these factors are pH, controlled by metering or dispensing pumps from reservoirs of acid or base, and temperature, controlled by several types of heating and cooling devices. These two parameters are unusual in that they are reversible in the same experiment (acid/base and warm/cool). Additives such as nutrients or inhibitors are reversible only through dilution, sequestration or metabolic activity. Microbial growth and growth rates can be followed, controlled or optimized by evaluating the light absorption response, or such other parameters as substrate utilization or metabolite production. The changing conditions can be single or multiple factors. For example, in a single fermentation experiment, the response of the growth rate of cells to a matrix of changes in pH and temperature with varying amounts of sodium chloride would yield a multidimensional map of the interactions among these three dependent variables. Thus, a single experiment would utilize critical points such as points of inflection, maxima and minima to determine the optima and minima of growth and growth rate as the conditions varied. Further, the system allows discovery of the existence of local maxima and minima. We believe that no previous combination of equipment and analytic logic could perform this experiment.

The system can ascertain the ability of cells to grow and degrade or produce materials in the course of varying the conditions of the fermentation. This instrument system will detect 1) the physiological shifts in end products and intermediates with varying such parameters as salinity, pH and temperature within a single fermentation, 2) short and long term effects on growth rates of varying pH, temperature and other variable parameters, and 3) the complex of relationships among these physiological parameters to disclose optima for desired end product or intermediate production. Feedback loops will allow actively changing conditions to slow growth and recover upon approaching the extremes of tolerance. Thus, the computer system will facilitate probing the tolerance physiology of various interacting parameters within a single fermentation experiment. In addition, the feedback loops can use the appropriate detectors (e.g., pH, Sodium ion, temperature, cell density as well as others such as fluoride, calcium, carbon dioxide, etc.) as control elements.

Bioreactor Parts

Bioreactor chamber: The chamber may take a number of forms depending on the nature of the organism and the goal of the fermentation. In many cases, a commercial chamber with glass walls (e.g., Bellco, New Brunswick Scientific, Ward's Natural Science, LabKorea, Infors, and Kontes) is needed. The top of the vessel accepts a flat, rigid head plate with fittings for introduction of probes, stirring shafts, etc. or may be made of all glass with multiple vertical side arms to accommodate the probes. The dimensions of the vessel may be of any size consistent with the liquid volume and number of entry and exit ports necessary to accommodate the desired fermentation protocol. Other materials may be substituted for glass, such as stainless steel, plastics, and the like. For some fermentation protocols, the vessel need not be resistant to autoclaving if the fermentation is unlikely to become contaminated. For example, fermentations with high saline conditions will minimize confounding contamination. In other cases, the fermentation with a large starting population of cells yields the desired information before contamination becomes significant. Such a cheaper chamber was used to successfully perform the fermentation described in Example 1.

Figure 10:
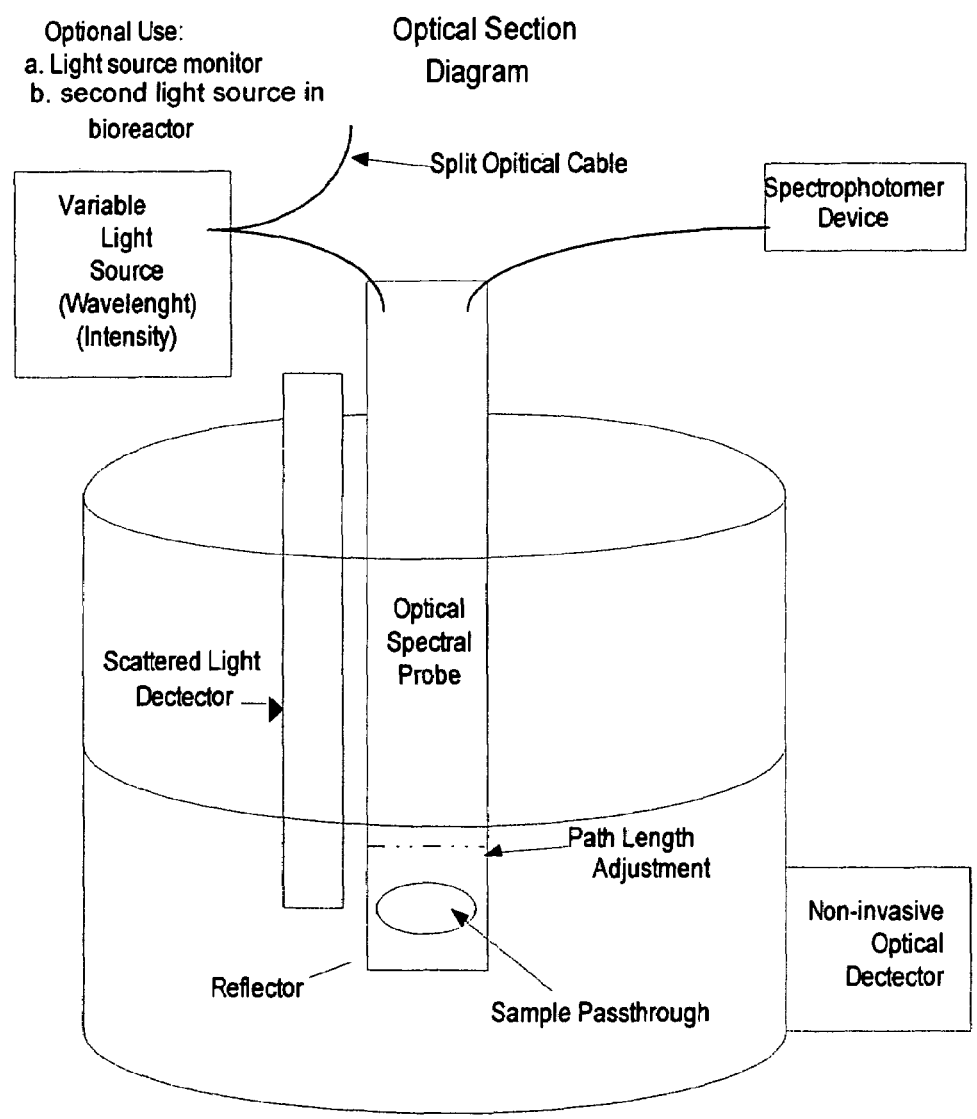
FIG. 10. Schematic diagram of the major components of the optical system.

Optical system: Complex spectral studies are preformed in the bioreactor with a small spectrophotometer fitted with a probe (e.g., Ocean Optics, Stellarnet). The dual optical fiber probe (or in some case several fiber paths) use one optical path to bring light into the reactor, and the other to transmit the modified light (by the bioreactor medium) to the spectrophotometer. A third path uses a beam splitting arrangement to lead a portion of the source light to a second spectrophotometer or light meter to monitor the source light for fluctuations. FIG. 10 schematically illustrates the optical system. Solid light pipes can replace the fiber optics. The path or distance that the light travels in the medium normally is fixed with a reflective surface attached to the probe. This distance defines the gap through which the test material flows, and allows the light to interact with the biological entity of interest.

Omitting the reflective surface allows spectral measurements of the components of a liquid sample without submerging the probe. In this embodiment, the entry and exit fiber paths do not necessarily need to be in the same probe. The exit fiber is coupled to a small spectrophotometer and where the light signal is filtered or spread into individual components by a diffraction grating. In the current embodiment, the filtered or spread components are received by individual photodiode elements (2048 for example) in a linear array that covers the wavelength spread of the grating. In a typical arrangement, the spread is 200 nanometers (nm) to 1000 nm which covers visible wavelengths, some ultraviolet and borders on the infrared. This allows for a spectral resolution of about 1200/2000 or 0.6 nm/diode (representing a spectral line). This device can be multi-scanned over time, to compare very specific parts of the spectrum by ratio or difference and the spectral peaks can be followed. The intensity of each spectral line can be saved in a spread sheet for further refinement. Additional probes can extend the spectrum further into the infrared by use of diamond optics for detection of specific spectral signatures.

For some simple optical applications such as following the growth of cells or determining changes in concentration of abroad spectrum pigment a less expensive optical device will suffice. We designed this low cost alternative by adapting a small solid state light sensor. This light sensor is a programmable color light-to frequency converter which combines configurable silicon photodiodes and a current-to-frequency converter on a single monolithic CMOS integrated circuit. The output is a square wave and frequency directly proportional to light intensity (irradiance). The full-scale output frequency can be scaled by one of three preset values via two control input pins.

Further details of the less are expensive device follow. The J light pipe with a micro-controlled programmable color to frequency converter chip (using a basic element supplied by TAOS, for example) and contains 64 photodiode elements. These elements are divided into 4-spectral sections, blue filter, green filter, red filtered and clear or no filter. The J light pipe is divided into two sections: the (J) section or detector section, and the (I) section or light section. The material is either glass or quartz for use in the ultraviolet. There is a gap between the two sections to accommodate the liquid fermentation medium. The air tips of the two sections (J and I) interface to the detector and the light respectively. The light normally is a full spectrum light source., e.g., a white solid state light emitting diode (LED), halogen, tungsten, etc. or, in special applications, a source emitting specific wavelengths. The detector, through the microcontroller, can switch between the three spectral regions or view the full spectrum as limited by the detector and light source. This allows various combinations of the spectrum to be utilized for differences or ratios. As an alternative to the light pipe the detector and LED can be placed directly in the liquid with a gap between them, and cold sterilization would be used as a substitute for autoclaving.

Sensors: Many commercial sensor probes are available for use in bioreactors (e.g., Sensorex, Brinkmann Instruments, Fluka, Adinstruments, Beckman, Omega, or many other sources such as the manufacturers of laboratory or commercial fermentation equipment. Many specialized probe sensors cannot be sterilized by heat. However, various chemical sterilizing agents may be used. In addition, biomolecules such as enzymes may be incorporated into sensing electrodes as exemplified by the research at NIST. Commercial vendors, such as Universal Sensors, Inc., supply some enzyme electrodes. Others that are suitable may be constructed by those skilled in the art.

Materials for which no usable commercial probe exists: The system can be used to study, in approximately real time, degradation or production of materials for which no probe currently exists. Two solutions of this problem are: 1) construction of specific immobilized enzyme electrodes for in situ measurement, or 2) ex situ, but rapid, measurement using a mass spectrometer or a gas chromatography-mass spectrometer as a more generalized detection system. The advantages of an immobilized enzyme electrode are high specificity including differentiating stereoisomers and rapid response allowing use in control loops. The disadvantages are problems in sterilization and short life. The advantages of a mass spectrometer are high chemical specificity (but not stereospecificity), versatility, and ability to detect many materials simultaneously in small samples. The disadvantages include technical and programming complexity, and the requirement to physically remove samples from the fermentation. The size of the sample may be negligible compared to the total volume. However, the time lag may preclude use of the results in a control loop in rapidly changing fermentations. Important time lags result if the sample must be extracted, derivatized, and/or run through a gas chromatographic column prior to mass spectrometry.

Interface electronics (Power supply/data acquisition): The initial embodiment unit uses a single National Instrument board internal to the Windows-based PC for data acquisition and control signals. Other devices, both internal and external may be used. The advantage of an external device is the ability to use various PC input/output channels such as USB, Firewire, serial, or parallel connections. Thus, any suitable PC or other computer may be used without the necessity of incorporating internal boards. The use of such general purpose interface electronics is to ensure that introducing a new configuration of sensors or controlled units such as pumps, stirrers, temperature regulators, light sources do not require unique interfaces or are not limiting in terms of realistic numbers.

Stirring: The preferred embodiment is utilization of a computer controlled stirrer introduced from the top. Many commercial sources for such a device exist. Alternatively, bottom driven magnetic stirrers often will be satisfactory.

Liquid introduction and removal: Digitally driven piston pumps are preferred where maximum accuracy and stop and go delivery is required. Digitally controlled peristaltic pumps are used where continuous flow, either in or out, and flow rate control is needed. Measurement of fluid volume by weight measure of variously, the liquid reservoirs or receiving vessels.

Software: The virtual instrument software utilizes LabView graphical software. There are numerous graphs, mathematical analysis, arrays and spreadsheets in this core prototype program. Also there is extensive use of virtual switching for functionality modification. The program is event driven such that the computer modifies the protocol of the fermentation upon the occurrence of specific events (e.g., points of inflection, achieving a set or calculated value of any data variable, or operator intervention). LabView is not a required software process control package. Further, the Windows operating system and Intel based computers are not requirements. Other commercial and open source software can be used such as Linux, Visual Basic, object oriented programs, or purpose built software in a variety of program languages. The key elements in the software are the ability to control and record data from a fermentation with or without operator intervention after start up and to obtain unique data and products (or suppress the generation of products) under computer supervision faster and at lower cost than with previous device-methods combinations.

The instrument is a stand-alone data collection and control station for the reactor mini lab system. The instrument collects data from sensors in analog and digital formats and also controls/records (under software direction) the many parameters involved for a complete bacteria based experiments for population growth/decay analysis. The instrument is a low cost and portable acquisition system that contains analog/digital data capture, analog output, and AC/DC power control. The instrument communicates with any off the shelf standard personal computer through the use of a USB (universal serial bus) connection. The USB bus system allows for connection of multiple instruments to a PC for multi-station experiments. We have designed and selected the USB based instrument to reduce the cost and complexity of a PC based acquisition and control system by bypassing the necessity to plug in expensive internal data acquisition subsystems inside the PC that are available on the open market.

Features of the instrument include at least the following:

8 single-ended, 4 differential 12-bit analog inputs 10 volt analog input range;

PGA with gains of 1, 2, 4, 5, 8, 10, 16, or 20 VN;

Up to 8 ksamples/sec (burst) or 1.2 ksamples/second (stream) 4 AC power outputs under program control 8 DC solenoid control outputs under program control supports software or hardware timed acquisition supports triggered acquisition;

2 analog outputs;

20 digital I/O (Up to 50 Hz per I/O);

32-bit counter;

Watchdog timer function;

Easy to use plug-and-play USB device;

Connect up to 80 instruments to one USB port complete software control, no jumpers or switches no power supply needed;

Includes application and driver software includes LabVIEW Vis; and

Works with Windows 98SE, ME, 2000, or XP.

The unique ability of broad spectrum capture is a basic tenet of the system. The creation of a database of spectra on the fly as the fermentation proceeds facilitates a number of important functionalities. All spectral changes are tracked and available for later interpretation. On the fly interpretations, presented graphically or in tables, include measures of cell density, following generation or disappearance of optically light absorbing materials, materials generating light through fluorescence or luminescence. Interpretations may include optical density, concentration, or intensity. The operator can choose one or more specific wavelengths and ratios among wavelengths for presentation in real time or as off-line interpretations from the fermentation database.

Operation of the system as a chemostat involves control of liquid input and output. The most precise method for implementing such control is through precision pumping. Most protocols involve constant volume in the fermentation vessel. The simplest method for such constancy is allowing excess volume to flow out of an exit port at the desired fluid level. In this implementation, the constancy is automatic, but typically cannot be changed during a fermentation session. Alternative methods allowing more flexibility, thus preferred, are to actively pump liquid from the fermentation. A triage valve, like those used in the refillable piston pumps, in the exit line allows diverting samples of the fermentation for offline analysis.

Using the optical probe without a reflector above the liquid surface, gives information on the relative intensity levels across the spectrum. The ratios of intensity levels estimate levels of an optically active solute when there is limited spectral contribution from other solutes in the liquid. More complex mixtures of optically active materials, including suspended particulates such as fat micelles or microorganisms, involve use of a variation of Beer's Law and multivariate mathematical analysis analogous to those for transmitted light spectra The difference is the requirement to calculate an "effective light path" from empirical data with known concentrations of material with known extinction coefficients.

Thus, the method to simultaneously determine concentrations of multiple soluble and suspended components in fluids wherein the components have different absorption or light scattering properties involve placing a light source over a liquid in a container such that light enters the fluid in the container. The light returning from the fluid in the container or collected from a side of the container, if transparent, is available for calibrating relative extinction coefficients of one or more components for application of Beer's Law in simultaneous equations or another mathematical model, thus, determining a concentration of one or more components of the material. The concentrations may be calculated either as static measurements or, as the sample container transits along a production line. The technique can determine simultaneous levels of components that either fluoresce naturally or can be coupled to fluorescing dyes. In addition to application to the bioreactor, the method is applicable analyzing samples of bodily fluids including serum from a clinical sample.

5. Microbiological Physiology & Mathematical Functions.

The growth behavior of the microbes or cells can be interpreted by the mathematical proprieties of the variations with time of the incoming data The changes in intensity of the light at the measured wavelengths are used for assessing luminescence or fluorescence. Optical Density measures changes in concentration. Where the extinction coefficient is known, Beer's Law is the mathematical function which yields absolute concentration. Further interpretation on the growth behavior results from application of such calculations as exponential functions, discontinuities, points of inflection, maxima, and minima. Growth and rates of growth of the bacterial are primary considerations. Any exponential base may be used as they are interconvertible. The most commonly used log scales are natural, base 2 and base 10.

Figure 11:
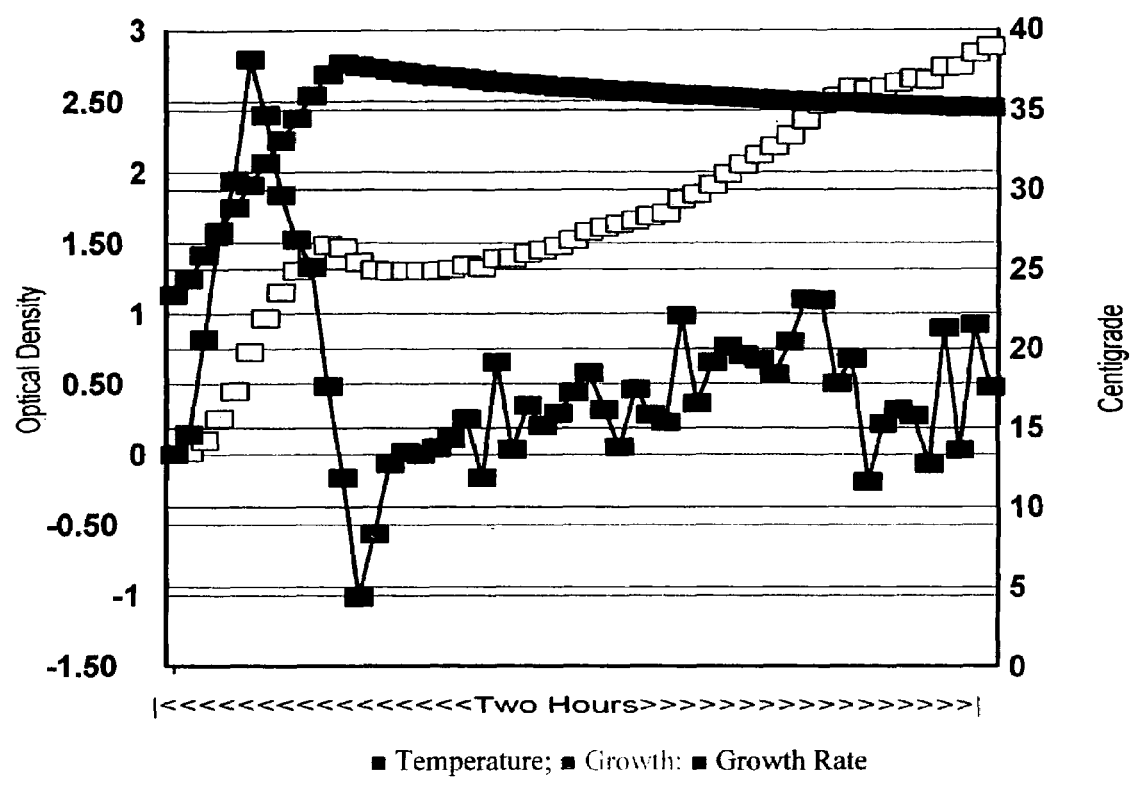
FIG. 11. Growth and Growth Rate were scaled to fit, and Growth Rate was calculated as the difference between adjacent OD readings.

Points of inflection (where the slope of a line changes from concave upward to concave downward or vice-versa) characterize maxima and minima. Points of inflection in the growth cycle indicate whether the bacteria are increasing their growth rate, maintaining their growth rate or decreasing their growth rate. As shown in FIG. 11, the rate switches from increasing to decreasing, the resultant point of inflection denotes the maximum growth rate found under the experimental conditions. If the base 10 exponential plot in FIG. 11 were converted to the base$_2$, the plot would indicate directly the instantaneous generation time (i.e., the time in which the population doubles) of the organism. This illustrates the ability of the invention to disclose transient phenomena.

The following examples illustrate embodiments of the invention, but should not be viewed as limiting the scope of the invention.

EXAMPLES

Optimum and maximum temperature: FIG. 11 illustrates the determination of the optimum and maximum growth temperature of a culture of the dairy bacterium, *Streptococcus lactis*. The time span of the graph is two hours. The heater was shut off after reaching the maximum growth temperature. The finding of optimum and maximum growth temperature occurred in considerably less than two hours as indicated by the clear maximum inflection point in the rate of growth. As the temperature drifted down, the growth rate slowly recovered. The effective maximum temperature is the temperature at which the growth rate becomes negative, i.e., the death of cells begins to exceed the growth. While cells continue to grow, the net effect of maintaining the temperature at any higher will lead to the death of all cells. The graph, for the first time, illustrates the determination of a much more precise optimum and maximum growth temperature and at considerably less cost in materials and especially labor compared to previous methods. In less than one hour, both optimum and maximum temperatures were determined.

Life in hypersaline environments as may exist on Mars: One of the most interesting groups of Eubacteria is the halotolerant group. These bacteria not only survive but grow over an extensive salinity range often from zero salt (or near zero) to 20 to 25% salt. At these higher salinities, available water is minimal and the organisms have evolved a range of survival strategies for these salinities. The primary strategy is the use of organic compatible solutes; most frequently ectoine (1,4, 5,6-tetrahydro-2-methyl-4-pyrimidinecarboxylic acid) and its derivatives, but also glycine, betaine, glycerol, trehalose. The osmoprotective solutes are either synthesized de novo or taken up from the environment. Such solutes must occur in high concentration in the cells to maintain adequate tonicity. Therefore, they are candidates as signatures for halophiles. Further, knowing the physiological conditions requisite for their uptake by these bacteria, their uptake in hypersaline environments could signify the presence of such halotolerant organisms. The digital bioreactor can determine the requisite conditions.

Halophilic Archaea maintain their osmobalance by concentrating potassium inside the cell to balance the external sodium levels. Thus, this group of organisms cannot be detected by searching for organic osmoprotective compounds. In addition to the physiological parameters of pH, temperature, and salinity, the changes in metabolism and growth of the halotolerant organisms induced by other materials possibly found in conjunction with hypersalinity such as magnesium, potassium, flouride, iron, and other mineral components would yield further candidates for signatures, including mineral depositions, especially in combination with organic material. This application describes a complex multiphasic system for use in the efficient study of the physiology of halotolerant and halophilic organisms to amass data leading to possible candidate signatures of life, past or present, in hypersaline environments on Mars.

The foregoing embodiments and advantages are merely exemplary and are not to be construed as limiting the present invention. The description of the present invention is intended to be illustrative and is not intended to limit the scope of the claims. Many alternatives, modifications and variations will be apparent to those skilled in the art. Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims.

The invention claimed is:

1. A device for determining and controlling cell growth or growth rate of cells in a fermentation reaction comprising:
    a fermentation vessel containing said fermentation reaction, wherein said vessel further comprises:
        a combination of sensors including at least a full-spectrum probe spectrometer or a multiple wavelength light-to-frequency converter, and pH and temperature sensors that measure a combination of conditions of said fermentation reaction in real time;
        a combination of controls of said fermentation reaction including at least a temperature control device; a stirring mechanism capable of completely mixing contents of said fermentation vessel; a metering or dispensing pump, and one or more variable-intensity, broad-spectrum light sources that radiate in at least the visible spectrum; and
        ports within said fermentation vessel for insertion of said combination of sensors and controls; and
    a computer configured for multiple function data acquisition from said combination of sensors;
    a data acquisition interface, which may be internal or external to the computer, that creates a digital pathway for said multiple functional data acquisition; and
    a software protocol that provides real-time instruction to said combination of controls based on said multiple function data acquisition by:
        (i) determining an optimum growth rate for the fermentation reaction at a set of established parameters by detecting an inflection point;
        (ii) oscillating a parameter of the set of established parameters;
        (iii) determining a growth rate tolerance value for the parameter to determine a decision criteria;
        (iv) looping back to step (ii) during the fermentation reaction by invoking an override function and repeating steps (ii) and (iii) for at least one other parameter of said set of parameters;
        (v) combining all decision criteria determined; and
        (vi) determining the cell growth or growth rate of cells in the fermentation reaction from the combined decision criteria.

2. The device of claim 1, wherein the digital pathway is selected from the group consisting of a USB, a firewire, a serial connection, and a parallel connection.

3. The device of claim 1, wherein the temperature control device is selected from the group consisting of a thermo-electrical heater or cooler, a resistance heater, and a double-jacket on the fermentation vessel for circulation of temperature controlled liquid.

4. The device of claim 1, wherein the light sources are light pipes.

5. The device of claim 4, wherein the light pipes include one or more J-type optical pipes.

6. The device of claim 1, wherein the temperature control device is a thermo-electrical heater or cooler.

7. The device of claim 1, further comprising one of more of a precise digital piston driven, step-up and step-down metering pump and at least one volume control pump.

8. The device of claim 1, further comprising at least one of a programmable AC power output, a DC solenoid control output, a differential sensor, a triggered-data acquisition, a timed-data acquisition, an analog output, a watchdog timer function, a flag function, or an interrupt function.

9. The device of claim 1, which detects and responds to physiological transient conditions within the vessel.

10. The device of claim 1, wherein the full-spectrum probe spectrometer detects visible, near infrared or near ultraviolet.

11. The device of claim 1, which is a chemostat and further comprises a nutrient concentration control, a pH control, and computer controllable digital or analog pumps for addition or removal of fluids from the fermentation vessel.

12. The device of claim 1, wherein the color light-to-frequency converter measures a spectrum of from 200 to 400 nm.

13. The device of claim 1, wherein an optical density measurement is made in a variable gap of a J-type optical pipe so that an LED or other light source can be mounted outside the fermentation vessel on the end of the light pipe.

14. The device of claim 1, which responses to conditions for detectable growth patterns and rates of growth based upon natural or programmable environmental changes.

* * * * *

UNITED STATES PATENT AND TRADEMARK OFFICE
CERTIFICATE OF CORRECTION

PATENT NO.         : 7,510,864 B2
APPLICATION NO. : 11/043431
DATED                  : March 31, 2009
INVENTOR(S)       : Krichevsky et al.

It is certified that error appears in the above-identified patent and that said Letters Patent is hereby corrected as shown below:

Revise Fig. 11 as attached to print as gray scale and with new line symbols for non-color printing. As shown on the attached page.

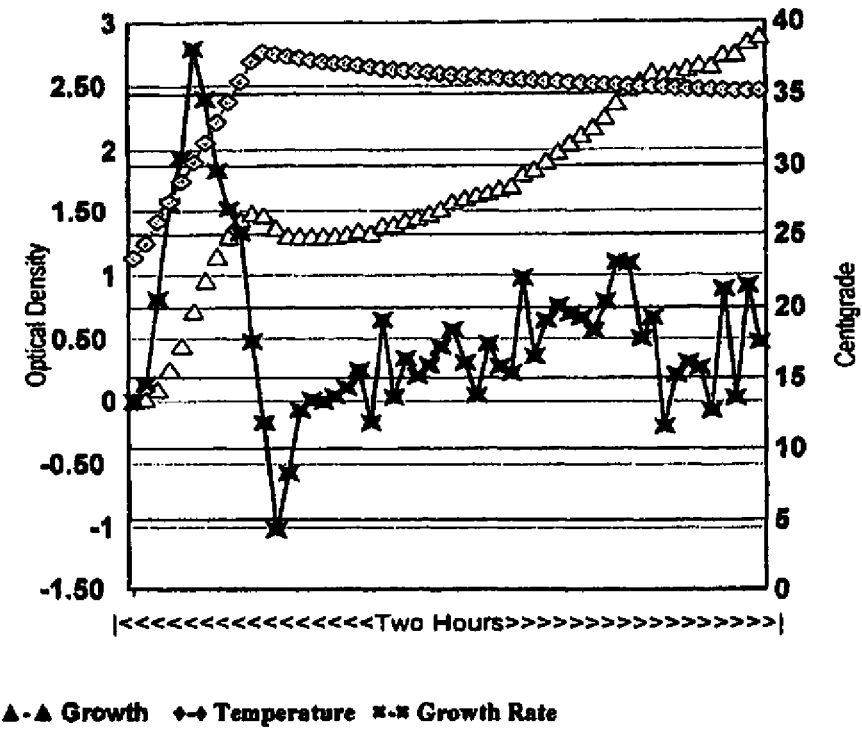

△-△ Growth   ◆-◆ Temperature   ✳-✳ Growth Rate

Figure 11

UNITED STATES PATENT AND TRADEMARK OFFICE
CERTIFICATE OF CORRECTION

PATENT NO.         : 7,510,864 B2
APPLICATION NO. : 11/043431
DATED               : March 31, 2009
INVENTOR(S)       : Krichevsky et al.

It is certified that error appears in the above-identified patent and that said Letters Patent is hereby corrected as shown below:

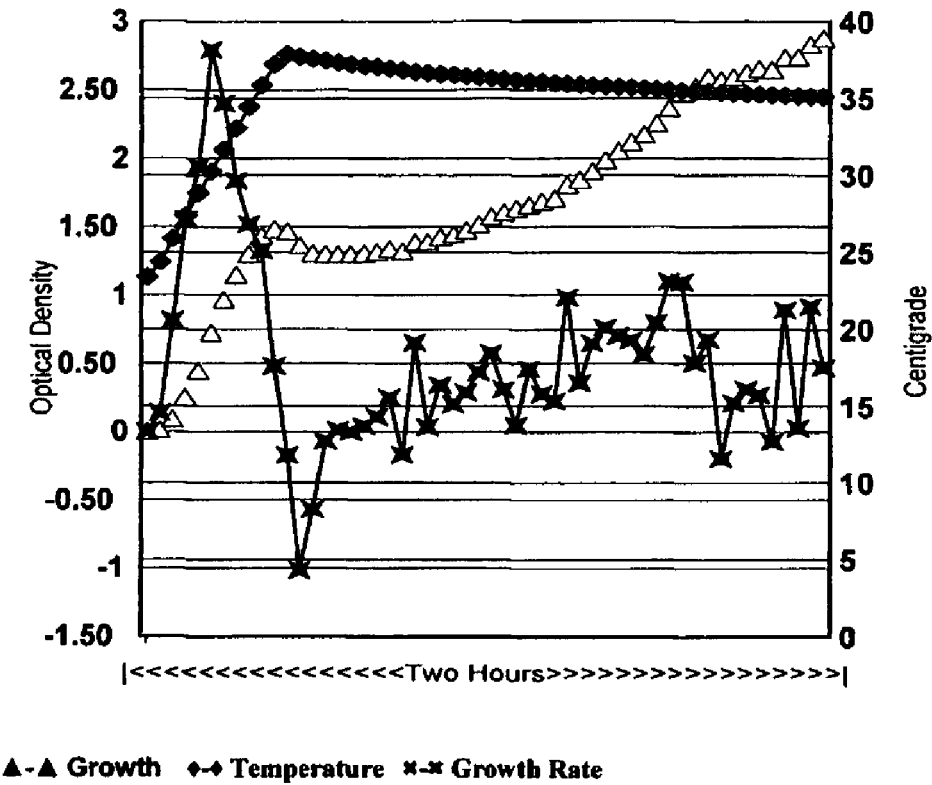

Figure 11

Signed and Sealed this

Fourteenth Day of July, 2009

JOHN DOLL
*Acting Director of the United States Patent and Trademark Office*